US009719705B2

(12) United States Patent
Fricking et al.

(10) Patent No.: US 9,719,705 B2
(45) Date of Patent: Aug. 1, 2017

(54) DISPOSABLE BIOREACTOR CONDENSER BAG AND FILTER HEATER

(71) Applicant: GE Healthcare Bio-Sciences Corp., Marlborough, MA (US)

(72) Inventors: Patric Fricking, Uppsala (SE); Parrish Galliher, Marlborough, MA (US); Geoffrey Hodge, Marlborough, MA (US); Michael Fisher, Woodstock, CT (US); Patrick Guertin, Mendon, MA (US); Richard Damren, Marlborough, MA (US); Colin Tuohey, Marlborough, MA (US); Thomas Erdenberger, Marlborough, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 0 days.

(21) Appl. No.: 15/131,790

(22) Filed: Apr. 18, 2016

(65) Prior Publication Data
US 2016/0231036 A1 Aug. 11, 2016

Related U.S. Application Data

(63) Continuation-in-part of application No. 13/434,345, filed on Mar. 29, 2012, which is a continuation of (Continued)

(51) Int. Cl.
*F25B 21/02* (2006.01)
*F25D 17/06* (2006.01)
(Continued)

(52) U.S. Cl.
CPC ............ *F25B 39/00* (2013.01); *B01D 5/0042* (2013.01); *B01D 5/0093* (2013.01); *C12M 23/28* (2013.01);
(Continued)

(58) Field of Classification Search
CPC .. B01D 5/0003; B01D 5/0015; B01D 5/0081; B01D 5/009; B01D 5/0042;
(Continued)

(56) References Cited

U.S. PATENT DOCUMENTS

3,212,274 A * 10/1965 Eidus ..................... F25B 21/04
165/110
5,372,621 A * 12/1994 Staton .................. B01D 53/265
55/319
(Continued)

*Primary Examiner* — Ryan J Walters
*Assistant Examiner* — Joseph Trpisovsky
(74) *Attorney, Agent, or Firm* — Grogan, Tuccillo & Vanderleeden, LLP (57) ABSTRACT

Disclosed herein is a system and method for condensing moisture in a moist gas stream entering a bioreactor or leaving a bioreactor, the system comprising: a condenser container capable of holding a fluid, the condenser container comprising: an outer wall surface and an inner wall surface, the inner wall surface defining an interior chamber for holding the fluid; and a first fitment attached to the outer wall surface of the condenser container, the first fitment forming a first port configured to allow the moist gas stream to flow through the first port and into the interior chamber; a second fitment attached to the outer wall surface of the condenser container, the second fitment forming a second port configured to allow a dried gas to flow from the interior chamber and out of the second port; and a cooling device in contact with at least one portion of the outer wall surface of the condenser container and arranged to cool the at least one portion of the outer wall surface of the condenser container, thereby to condense moisture in the moist gas stream and forming a dry gas stream for entering or leaving the bioreactor.

19 Claims, 6 Drawing Sheets

Related U.S. Application Data application No. PCT/US2010/050859, filed on Sep. 30, 2010.

(60) Provisional application No. 61/247,368, filed on Sep. 30, 2009.

(51) Int. Cl.
| | | |
|---|---|---|
| *F25B 5/00* | (2006.01) | |
| *F28F 7/00* | (2006.01) | |
| *F28F 3/12* | (2006.01) | |
| *F28F 3/14* | (2006.01) | |
| *F25B 39/00* | (2006.01) | |
| *B01D 5/00* | (2006.01) | |
| *C12M 1/00* | (2006.01) | |
| *F25B 39/04* | (2006.01) | |

(52) U.S. Cl.
CPC ............. *C12M 29/26* (2013.01); *F25B 21/02* (2013.01); *F25B 39/04* (2013.01)

(58) Field of Classification Search
CPC ..... B01D 5/0093; C12M 23/14; C12M 23/26; C12M 23/28; C12M 41/12; C12M 41/18; C12M 41/22; C12M 29/26
USPC .......... 62/315, 3.2, 3.4, 96, 93, 283; 165/46, 165/84, 104.15, 104.16, 104.19, 169, 170, 165/185

See application file for complete search history.

(56) References Cited

U.S. PATENT DOCUMENTS

| | | | |
|---|---|---|---|
| 6,572,641 B2 * | 6/2003 | Brugger | ............... A61F 7/0085 607/106 |
| 8,455,242 B2 | 6/2013 | Staheli et al. | |
| 9,127,246 B2 | 9/2015 | Staheli et al. | |
| 9,284,524 B2 | 3/2016 | Staheli et al. | |
| 2005/0272146 A1 * | 12/2005 | Hodge | ............... B01F 13/0827 435/289.1 |
| 2006/0279167 A1 * | 12/2006 | Turner | ..................... E03B 3/28 310/307 |
| 2008/0262409 A1 * | 10/2008 | Derrico | ................... A61M 5/44 604/19 |
| 2009/0311776 A1 * | 12/2009 | Kelly, Jr. | ............... C12M 23/20 435/289.1 |
| 2011/0207218 A1 * | 8/2011 | Staheli | ............... B01F 3/04241 435/394 |

\* cited by examiner

Fig. 5b

DISPOSABLE BIOREACTOR CONDENSER BAG AND FILTER HEATER

RELATED APPLICATIONS

This application is a continuation in part of U.S. application Ser. No. 13/434,345, which is a continuation of International Application No. PCT/US2010/050859, which designated the United States and was filed on Sep. 30, 2010, published in English, which claims priority to U.S. Provisional Patent Application No. 61/247,368, filed on Sep. 30, 2009. The entire teachings of the above applications are incorporated herein by reference.

FIELD OF INVENTION

The present disclosure relates to devices and methods for the use with disposable bioreactors or with non-disposable tank bioreactors.

BACKGROUND

Cell culturing is an essential step in manufacturing biological products, and may be carried out in disposable bioreactors systems or in non-disposable bioreactors such as steel tank vessels. Oxygen is continuously supplied to promote cell growth, and carbon dioxide is removed. A gas stream going to or coming from a bioreactor may contain moisture entrained within the gas stream. The moisture in the gas may condense as the gas passes through a filter or other system component. The moisture and/or condensation may be detrimental to the functioning of the filter or other system component.

A number of yet un-solved problems are inherent in currently available condenser designs for use with bioreactors. Some prior art designs incorporate several functionally different areas such as, for example, subducts and different cooling and heating zones, that result in a complex and costly assembly requiring special tooling, specially molded or machined components. Prior art designs also separate a vessel for condensate collection from the heat exchange area, thus adding complexity to the part instead of integrating condensate removal directly from the heat exchange zone. Because prior art designs are complex and tend to be expensive, such condensers are not truly disposable.

Another yet un-resolved problem inherent in many prior art condenser designs is that the heat is removed from the exhaust gas and then the heat is just wasted by pouring it into the environment to get rid of it.

Currently available condensers also may have another drawback inherent in the use of a multiplicity of ducts. Although the relatively long pathway provided by the many ducts increases the surface area of the condenser available for cooling, the decrease in cross-sectional area of a duct also increases the velocity of the gas flowing through the condenser, which in turn decreases the residence time of the exhaust gases in the condenser. The decreased residence time in the condenser results in a decrease in the overall cooling effect of the condenser on the exhaust gas within the condenser bag.

Yet another drawback of many currently available condensers is related to the inclusion of both a cooling zone and a heating zone within the condenser unit. Coupling the condensing function of the unit with a heating function within the same assembly reduces the flexibility of allowing the two functions to be manipulated independently of each other.

Thus, there is an on-going need for an improved apparatus, in particular, a truly disposable apparatus, and method that provide a means to reduce the moisture content of a moist gas within a bioreactor system before it is passed on to a filter or other system component where moisture and/or condensation on the filter or system component may interfere with the functioning of the filter or other system component.

BRIEF SUMMARY OF THE DISCLOSURE

The inventors of the present subject matter have now discovered a disposable bioreactor condenser that overcomes many of the problems found in the use of prior art condensers. The invention inter alia includes the following, alone or in combination. In one aspect, the present invention relates to our discovery of an apparatus and a corresponding method for condensing the water vapor in a stream of gas passing into or out of a bioreactor.

One embodiment of the invention is a system for condensing moisture in a moist gas stream entering a bioreactor or leaving a bioreactor, the system comprising: a condenser container capable of holding a fluid, the condenser container comprising: an outer wall surface and an inner wall surface, the inner wall surface defining an interior chamber for holding the fluid; and a first fitment attached to the outer wall surface of the condenser container, the first fitment forming a first port configured to allow the moist gas stream to flow through the first port and into the interior chamber; a second fitment attached to the outer wall surface of the condenser container, the second fitment forming a second port configured to allow a dried gas to flow from the interior chamber and out of the second port; and a cooling device in contact with at least one portion of the outer wall surface of the condenser container and arranged to cool the at least one portion of the outer wall surface of the condenser container, thereby to condense moisture in the moist gas stream and form a dry gas stream for entering or leaving the bioreactor.

Another embodiment of the invention is a method of condensing moisture in a moist gas stream leaving a bioreactor, the method comprising: providing a system as disclosed in the preceding paragraph; providing fluid communication of the first port of the condenser container with or between a port of the bioreactor arranged to allow the moist gas stream to leave the bioreactor; allowing the moist gas stream leaving the bioreactor to flow through the first port and into the interior chamber of the condenser container; cooling the at least one portion of the outer wall surface of the condenser container; allowing heat to be transferred from the interior chamber of the condenser container to the cooling device, thereby lowering the temperature of the interior chamber of the condenser container; condensing moisture in the moist gas stream; and forming a dry gas stream leaving the bioreactor.

A gas stream leaving a bioreactor typically is passed through a filter. A moist gas would clog the filter. The dry gas stream formed according to an embodiment of the invention will not tend to clog the filter.

In one embodiment, the condensate can be collected and either returned to the bioreactor, sent to another device, or discarded. For example, in one embodiment, the condenser container in the disclosed system for condensing moisture in a moist gas stream may comprise a fitting such as a hose barb for attaching and securing tubing to collect condensate for either a gravity flow of the condensate or a pumping of the condensate from the interior chamber and back into the bioreactor.

Another embodiment of the invention is a method of condensing moisture in a moist gas stream to form a dry gas for addition to a bioreactor, the method comprising:

providing a system as described herein; providing fluid communication of the first port of the condenser container with the moist gas stream; allowing the moist gas stream to flow through the first port and into the interior chamber of the condenser container; cooling the at least one portion of the outer wall surface of the condenser container; allowing heat to be transferred from the interior chamber of the condenser container to the cooling device, thereby lowering the temperature of the interior chamber of the condenser container; condensing moisture in the moist gas stream; thereby forming a dry gas.

The dry gas formed by the disclosed method can then be flowed out of the second port and into a bioreactor.

The cooling device may also include a heating source arranged to provide heating of a filter within the bioreactor. The cooling device may include a thermoelectric module such as, for example, a Peltier heating and cooling module.

BRIEF DESCRIPTION OF THE DRAWINGS

The foregoing and other features and advantages of the invention will be apparent from the following more particular description of illustrative embodiments of the invention, as illustrated in the accompanying drawings. The drawings are not necessarily to scale, emphasis being placed upon illustrating the results of exemplary embodiments of the disclosed apparatus.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The invention relates to a system that performs at least one specific function for a bioreactor. The function may be condensing moisture within a gas stream entering or leaving the bioreactor, or it may be heating a filter to prevent condensation within the filter.

We have now discovered a condenser system that utilizes a cooling device to power a disposable bioreactor condenser. The disclosed system may include a filter heater that utilizes heat from a thermoelectric heating and cooling system. Any cooling device could be used in an embodiment of the invention. For example a liquid coolant circuit, a vapour compression refrigerator or a cold gas stream. In a preferred embodiment, the cooling device is a thermoelectric cooling device. A thermoelectric cooling device includes a solid-state method of heat transfer through dissimilar semiconductor materials. Thermoelectric cooling is referred to as "the Peltier Effect," after Peltier, an experimental physicist who discovered the phenomenon in 1834. If a current is passed through a thermocouple, heat is absorbed (or removed) at one junction and is evolved at the other junction of the thermocouple. If the first junction is in a closed region, the first region will be cooled.

We used a thermoelectric Peltier module (TE Technology, Inc., Traverse City, Mich.) to power a disposable bioreactor condenser and filter heater. In general, a thermoelectric Peltier module operates to cool one surface of the module, and the heat removed from the cooled side is transferred to the other hot side of the thermoelectric module. In an embodiment of this invention both the heated side and the cooled side of the thermoelectric Peltier module are used. The cooled side of the Peltier module provides the cooling for the condenser function of the invention, while the heated side of the Peltier module can be used to assist in heating of a filter. In most commonly seen applications using a thermoelectric Peltier cooling module, the heat generated on the heated side of the thermoelectric Peltier module is conducted away from the system as waste heat and is not used. With a slight modification of the disclosed system, that heat can be used for heating a filter. Heating the filter tends to convert any condensed water droplets into the vapor phase so that the condensate does not clog the filter.

In one embodiment of the invention, the condenser container is a single use, flexible, nonporous bag comprising a flexible polyethylene material or film. The condenser container in most of the embodiments described herein is referred to as a "bag" or a "condenser bag" or a "flexible bag." However, other embodiments of the invention may include a rigid or a semi-rigid container instead of a flexible bag. The condenser bag may comprise two sides, a front panel and a back panel, as in what is known as a "two-dimensional bag," or it may be a three-dimensional bag or have any other suitable shape and size.

The condenser bag may have fitments attached to it. The term "fitment" as used herein refers to a separate object that is heat-welded to the flexible bag film in order to attach it. As such, a fitment often comprises a polymeric material which can be the same or similar to the polymeric material comprising the wall of the flexible bag. A fitment is often a more dense material than the wall of the flexible bag, and may be added to the bag to enable a functionality. A non-limiting example of a fitment is one that forms a port. In one embodiment of the invention, a port is added to the wall of the condenser bag in order to allow gas to enter. In another embodiment of the invention, a port is added to the wall of the condenser bag to allow gas to leave the condenser bag.

Figure 1A:
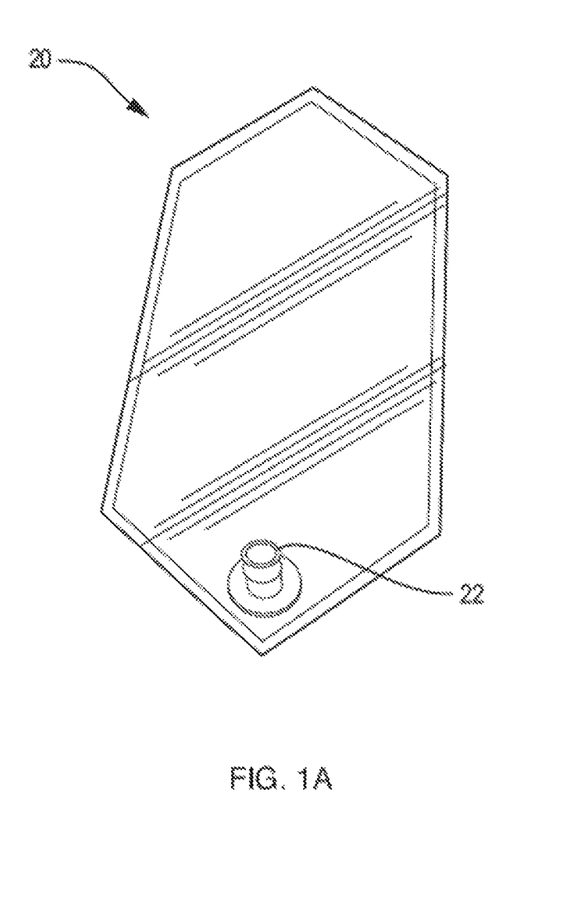
FIG. 1A is a schematic drawing of a perspective view of a prototype two-dimensional disposable bioreactor condenser bag according to an embodiment of the invention.

In one embodiment of the invention the condenser bag comprises a nonporous polymeric material that is biocompatible with the cells and medium used for cell growth in a bioreactor. FIG. 1A is a schematic drawing of a perspective view of a prototype disposable bioreactor condenser bag 20 according to an embodiment of the invention. The prototype condenser bag 20 is shown with one fitment 22 for a port. A condenser bag according to an embodiment of the invention can have a plurality of fitments and ports. The embodiment depicted in FIG. 1A does not have any structure within the bag to promote turbulence or condensation.

Figure 1B:
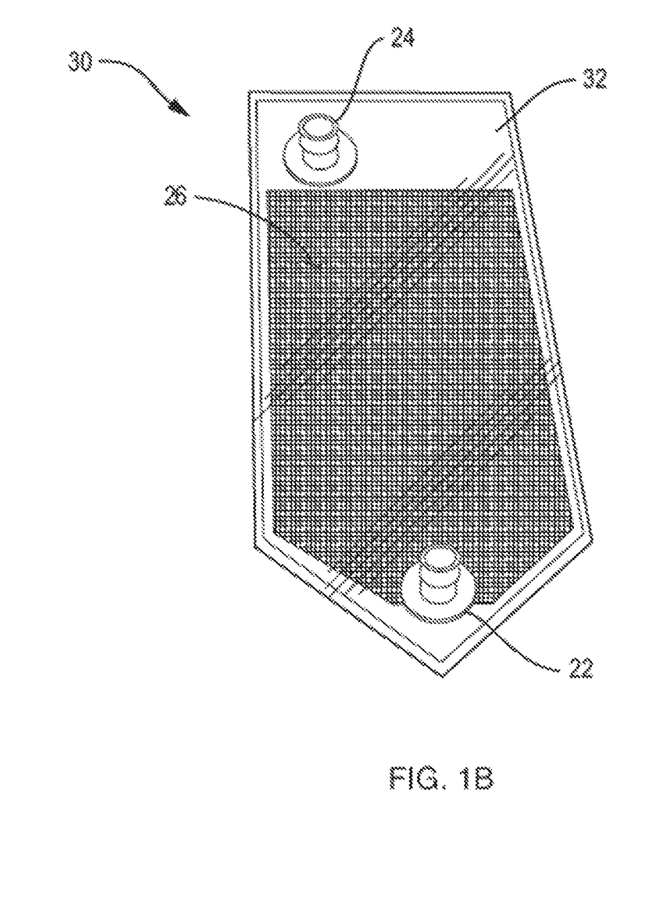
FIG. 1B is a schematic drawing of a perspective view of a two-dimensional disposable bioreactor condenser bag according to an embodiment of the invention, having mesh disposed within the condenser bag and visible through the bag film.

FIG. 1B is a schematic drawing of a perspective view of a disposable bioreactor condenser bag 30 according to an embodiment of the invention. The mesh 26 disposed within the condenser bag 30 is visible through the top surface 32 of the bag film. Two fitments 22, 24 are shown on the outer wall of condenser bag 30. In one embodiment of the invention, fitment 22 is used for forming an inlet port for moist gas and fitment 24 is used for forming an outlet port for dried gas. In another embodiment, fitment 22 can be used to form an outlet and fitment 24 an inlet. In one embodiment the condenser bag 30 is disposable.

The condenser bag 30 is used in conjunction with a cooling source to lower the temperature of a moist gas stream going to or coming from a bioreactor such that condensation of moisture entrained within the gas occurs within the condenser bag 30. This condenser bag 30 can be used to reduce the moisture content of the moist gas before it is passed on to a filter or other system component where moisture and/or condensation may be detrimental to the functioning of the filter or other system component.

In one embodiment, the disposable condenser bag 30 forms a closed volume that has at least one inlet fitment 22 to allow for a moist gas to be flowed into the condenser bag 30 from a bioreactor or from another gas source, and at least one outlet fitment 24 to allow for the passage of the dry gas stream out of the condenser bag 30. The condenser bag 30 may include an internal arrangement of a biocompatible material such as mesh 26 within the closed volume that will promote the condensation of moisture from the gas passing through the condenser bag 30, and also increase the turbulence within the gas stream as it passes through the condenser bag. In one embodiment of the invention, the mesh 26 or other biocompatible material is pleated to provide increased contact of the moist gas stream with the mesh such that it substantially completely fills the gap between the two inner layers of the condenser bag 30.

In another embodiment of the invention, the structure arranged to allow condensation to form thereon, and/or to increase turbulence is a series of fins attached to a support. In yet another embodiment the structure arranged to allow condensation to form thereon comprises a spiral coil. Any structure within the bag that can promote turbulence and/or promote condensation is within the scope of the invention.

Non-limiting examples of materials suitable for forming the structure for promoting condensation within the condenser bag 30 include polyethylene, polypropylene, polyester, polyamide, and a metal.

At least one surface of the condenser bag 30 is in contact with an external cooling source, for example, a cold plate, which by conduction cools at least one surface, for example top surface 32 of the condenser bag 30, which in turn cools the inside surface of the bag 30 and cools the moist gas stream to or below its dew point temperature as the gas flows over the cooled surface.

Figure 2:
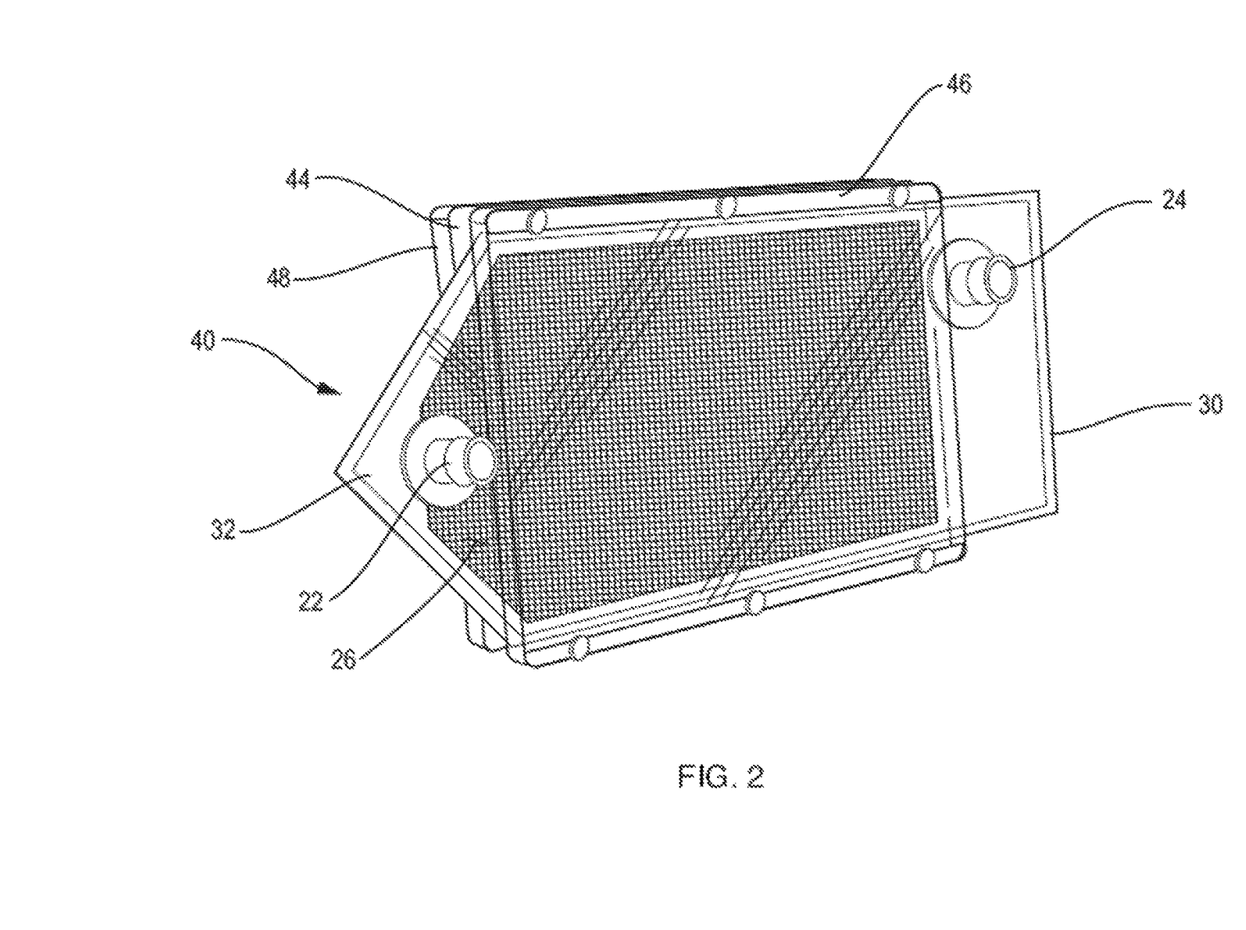
FIG. 2 is a schematic drawing of a perspective view of a system according to an embodiment of the invention, the system utilizing a thermoelectric heating and cooling device for condensing moisture in a gas stream entering or leaving a two-dimensional bioreactor.

FIG. 2 is a schematic drawing of a perspective view of a system 40 according to an embodiment of the invention for condensing moisture in a gas stream entering or leaving a bioreactor. The disposable bioreactor condenser system 40, which may include a filter heater system according to an embodiment of the invention, comprises several major functional components. The components of the system include the disposable bioreactor condenser bag 30, a cold plate, a thermoelectric Peltier module with associated controller, a cold plate/condenser bag holder or frame 46, 48, and a filter heater enclosure (not shown).

In FIG. 2, the system 40 as shown includes a condenser bag front frame holder 46 and a condenser bag back frame holder 48, the frame forming a sandwich with the condenser bag 30 held firmly against a cold plate. The cold plate (not shown) is positioned on surface 44 of the back frame holder 48.

In a preferred embodiment, a cold plate appropriately sized to approximately match the surface area of one side of the condenser bag 30 is attached to the cold side of the thermoelectric Peltier module to maximize its contact area with the disposable condenser bag. In one embodiment of the invention, provision is made on the cold plate to provide a means of securing the disposable condenser bag 30 in position on the cold plate in order to ensure that at least one surface of the disposable condenser bag 30 is in contact with the cold plate surface.

In another embodiment of the invention both a front panel and a back panel of the disposable container are in contact with a cold plate surface, i.e. the condenser bag is squeezed between at least two plates comprising thermoelectric modules.

The condensate generated within the condenser bag 30 can be drained from the bag continually or periodically. The condensate that collects within the condenser bag 30 may be drained through an inlet port fitment 22. Alternatively, there may be a separate fitment, for example, a hose barb (not shown) attached to a surface of the condenser bag specifically for draining the condensate. The hose barb may be used for attaching and securing tubing to collect condensate for either a gravity flow of the condensate or a pumping of the condensate from the interior chamber of the condenser bag and back into the bioreactor. This recycling of the liquid water may be utilized to maintain constant volume of the liquid and constant osmolarity within the bioreactor.

Alternatively, the condensate may be sent to another storage device as required by the bioreactor process being used or it may be discarded.

The hot side of the thermoelectric Peltier module generates heat that can provide or assist in the heating of a filter to keep its temperature above the dew point temperature of the gas that is flowing through the filter. With no more than routine experimentation, a suitable enclosure or ducting structure can be devised and attached to the hot side of the thermoelectric Peltier module to allow the heat generated to be directed to the filter in such a manner as to heat or assist in the heating of the filter. The heat may be actively directed to the filter by use of a fan or may be passively directed to the filter using convection, or a suitable combination of the two methods may be used.

Figure 3:
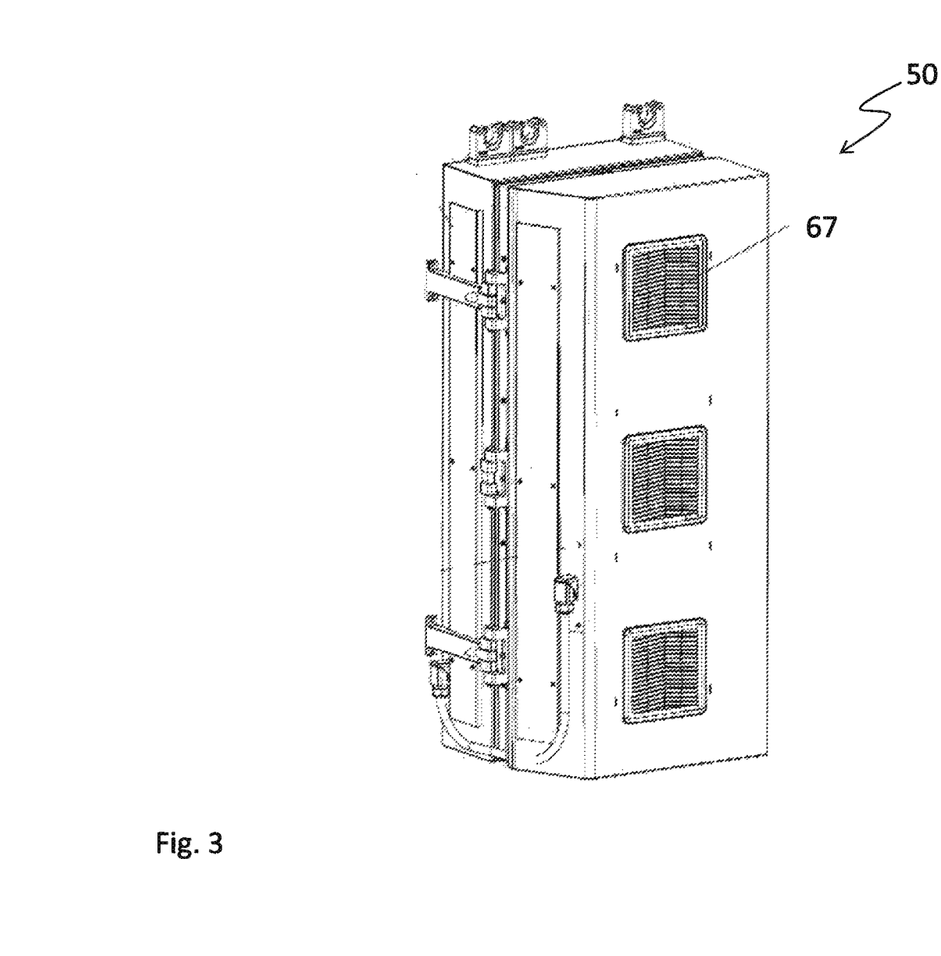
FIG. 3 is a schematic drawing of a perspective view of a system according to an embodiment of the invention.
Figure 4:
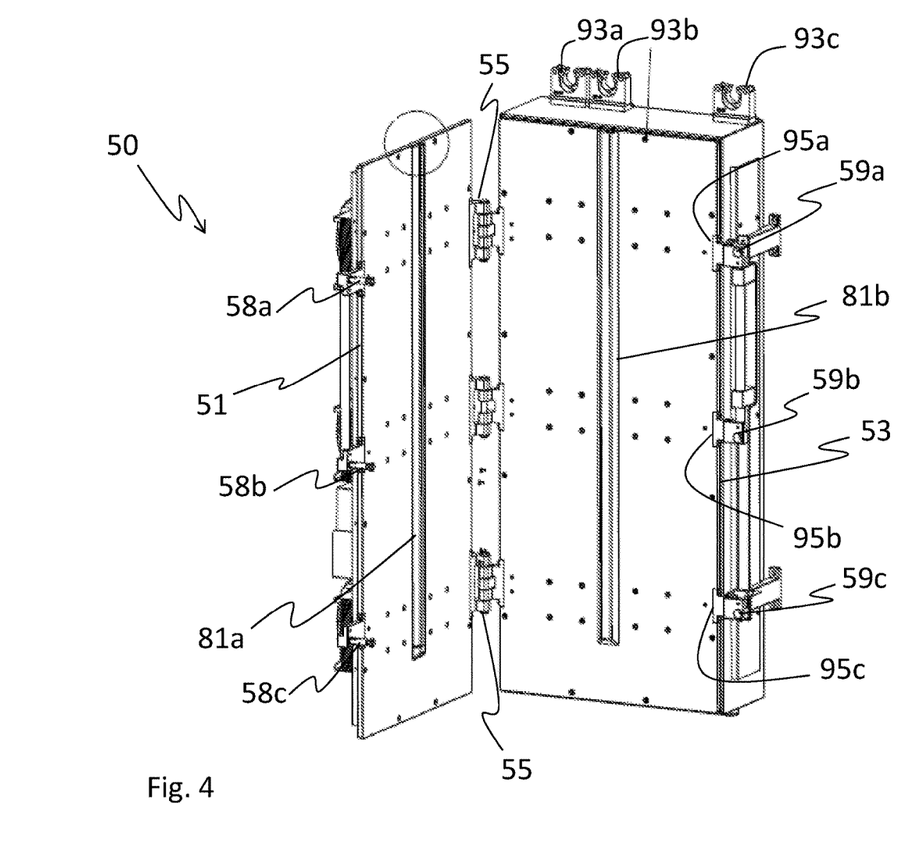
FIG. 4 is a schematic drawing of a perspective view of the system shown in FIG. 3 in an open position for loading of a condenser container.
Figure 5A:
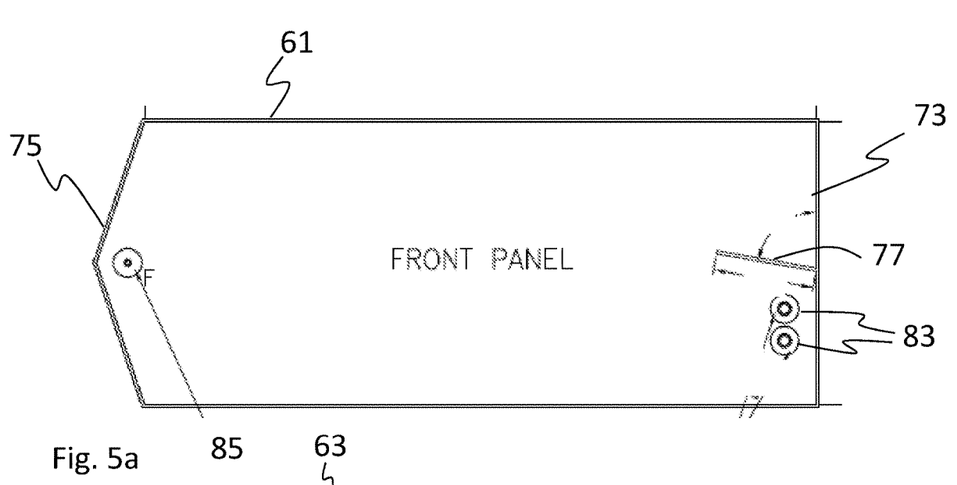
FIG. 5a is a schematic drawing of a front panel of a condenser container according to one embodiment of the invention.
Figure 5B:
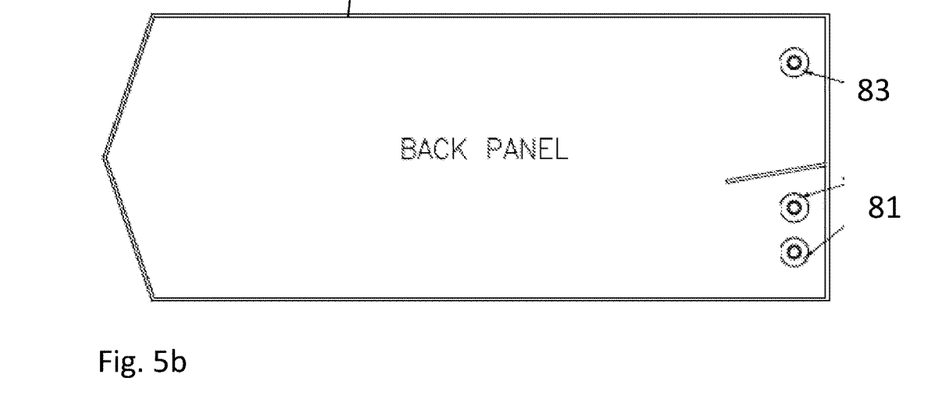
FIG. 5b is a schematic drawing of a back panel of a condenser container according to one embodiment of the invention.
Figure 6:
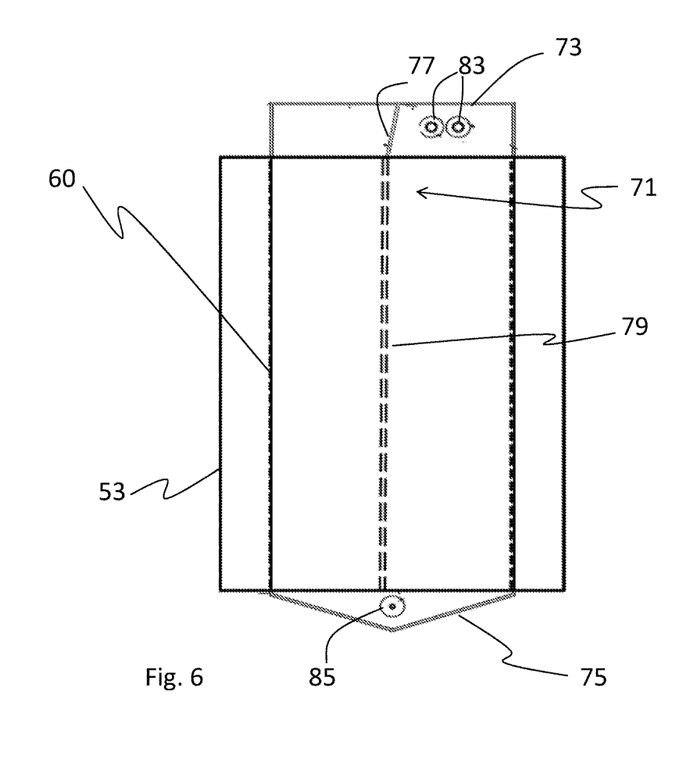
FIG. 6 is a schematic drawing of a condenser container when provided on a second plate of the system.

FIGS. 3-6 show schematically a system 50 according to one embodiment of the invention. FIGS. 3 and 4 show the system 50 without a condenser container provided in the system. FIGS. 5*a* and 5*b* show a front panel 61 and a back panel 63 of a condenser container 60 according to one embodiment of the invention. FIG. 6 shows schematically a condenser container when provided on a second plate of the system. The system 50 comprises a first plate 51 and a second plate 53. The back panel 63 of the condenser container is arranged to be provided against the surface of the second plate 53 when the condenser container 60 is provided in the system 50 as shown in FIG. 6. The first plate 51 is connected to the second plate 53 by hinges 55 along one of its sides. Hereby the system can be opened and closed for the installation and removal of a condenser container. The front panel 61 of the condenser container is arranged to be provided against the surface of the first plate 51 when the first plate 51 is closed, i.e. swiveled around the hinges 55 into a position in front of the second plate 53. A locking mechanism is in this embodiment provided for locking the first plate 51 in a closed position. In this embodiment three locking pins 58*a*, 58*b*, 58*c* are provided to the first plate 51 along a side opposite the hinges 55 and three corresponding openings 59*a*, 59*b*, 59*c* are provided to the second plate 53 along a side opposite to the hinges 55. Furthermore a locking mechanism 65 is provided which can lock the three pins in the three openings and release them suitably by one single action. This could for example be provided by a rod passing all three openings 59*a,b,c*. The rod is provided with openings for the pins 58*a,b,c* and with pin locking means which will lock the pins in the openings when the rod is moved downwards. The pin locking means could be protrusions provided above each opening in the rod and arranged to be engaging a corresponding groove in the pins when the rod is moved downwards. The rod could be moved downwards by its own weight or by an action from an operator. The rod can then be moved upwards by an operator for releasing the pins from the locked position in the openings.

A cooling device, for example in the form of at least one thermoelectric module, is in this embodiment attached to both the first plate 51 and to the second plate 53. Hereby both a front panel 61 and a back panel 63 of the condenser container will be cooled. In one embodiment of the invention three thermoelectric modules 67 are attached to the first plate 51 and three thermoelectric modules are attached to the second plate 53. In FIG. 3 the system 50 is shown in a closed position and here a ventilation opening for each of the thermoelectric modules 67 provided to the first plate 51 can be seen. The size of the system 50, the number of thermoelectric modules, the number of locking pins 58 and corresponding openings 59 and the number of hinges 55 can of course vary.

The condenser container 60, when held in the system 50, is provided with a partition 71 substantially in the middle of the container and starting from a first side 73 of the container towards an opposite second side 75 of the container but not all the way to this opposite second side, thus leaving an open passage at the opposite second side. This can be schematically seen in FIG. 6. The partition 71 is a welding 77 in the condenser container 60 and/or a compression 79 provided to the condenser container by at least one bar 81*a*, 81*b* provided to at least one of the first or second plates 51, 53, said bar 81*a*, 81*b* being arranged to provide a partition to the condenser container by compressing the condenser container against the other of the first or second plates. In the embodiment shown in FIGS. 3-6 a first bar 81*a* is shown provided on the first plate 51 and a second corresponding bar 81*b* is provided on the second plate 53. The bars 81*a*, 81*b* will together compress the container when a container is provided in the system and the system is closed. In the embodiment shown in FIGS. 3-6 the partition 71 comprises both the compression 79 provided by the at least one bar 81*a*, 81*b* and a welded part 77 in the condenser container 60 meeting each other. Said welded part 77 is provided from a first side 73 of the condenser container 60 and provided inclined towards the compression 79 from the at least one bar such that the welded part 77 and the compression 79 together form a partition 71 from the first side 73 of the condenser container 60 towards the opposite second side 75. The inclination of the welded part 77 provides an acceptance for slightly different positioning of the condenser container between a first plate 51 and a second plate 53 when a condenser container 60 is provided in the system 50. Because of the inclination the welded part 77 and the compression 79 will still meet and provide a complete partition 71 together. The first and second sides 73, 75 of the condenser container are in this embodiment protruding out from the first and second plates 51, 53. This is suitable because ports provided to the container close to the first and second sides of the container can be provided outside the first and second plates and will be easier to access by a user. However, in another embodiment of the invention the partition 71 could instead be welded in the container all the way. In that case no compression bars are needed. Another possibility can be to design the first and/or second plates to open up for the ports of the container. In that case the partition 71 can be provided all the way from the first side of the container by compression from the at least one bar and no welded part is needed.

In FIGS. 5*a*, 5*b* and 6 it can be seen that a number of ports, also called fitments, are provided to the condenser container 60. At least one first fitment 81 is attached to the outer wall surface of the condenser container 60 close to a first side 73 of the container on one side of the partition 71 and at least one second fitment 83 is attached to the outer wall surface of the condenser container 60 close to the first side 73 of the container but on the other side of the partition 71. However, the fitments/ports could as well be attached, for example welded, to an inner wall surface of the condenser container. In the embodiment shown in FIGS. 5*a* and 5*b* five ports are shown close to the first side 73 of the condenser container. Three of them are provided to the back panel 63 and two of them to the front panel 61. However, the number and positions of ports can be varied. At least one first port 81 for allowing gas to flow into the container is needed and at least one second port 83 for allowing gas to flow out of the container is needed and the at least one port for inflow of gas should be provided on one side of the partition 71 and the at least one port for outflow of gas should be provided on the other side of the partition. In the embodiment shown in FIGS. 5*a* and 5*b* the partition 71 comprises both a welded part 77 and a compression part 79. The ports 81, 83 are provided on one side each of the welded part 77. These first and second ports 81, 83 will be provided above the first and second plates 51, 53 when the container is provided in the system. Furthermore, a condensate drain port 85 may be provided close to the opposite second side 75 of the container 60. Through this condensate drain port 85 condensate can be taken out from the container. The partition 71 and the position of the first and second ports 81, 83 on each side of the partition 71 will provide a flow of the gas in the container from the first side 73 of the container, to the second side 75 of the container and back again to the first side 73 but on the other side of the partition 71.

Tubes can be connected to the ports 81, 83 of the of the condenser container. These tubes can be secured into tube holders 93*a*, 93*b*, 93*c* which are provided to an upper part (referring to directions in the FIGS. 3 and 4) of the system. Hereby the condenser container 60 can be kept in a correct position during installation. Furthermore the right long side of the condenser container 60 (referring to directions in FIGS. 3 and 4) can be squeezed into notches 95*a*, 95*b*, 95*c* provided at the right long side of the second plate 53. Hereby the condenser container can be kept in a correct position.

The relatively large cross-sectional area of a condenser bag according to an embodiment of the disclosed invention increases the residence time of the moist gas within the condenser container as compared to the residence time of a moist gas in a prior art system using a pathway of ducts. This is because the velocity of the gas stream is increased in a narrowed passageway such as a long duct. In the embodiment of FIGS. 3-6, the large cross-sectional area is preserved while the flow path is of U shape. By arranging the condensate drain port 85 at the lower portion of the U shaped flow path, effective drainage is achieved. By including a mesh or other biocompatible material inside the large cross sectional area of the bag to enhance condensation, we achieved similar or improved results at a much lower cost than that of a system with extensive ductwork.

The mesh or screen material in a condenser bag according to an embodiment of the invention serves several functions. First, the mesh increases turbulent flow within the bag which ensures that the moist gas comes into contact with the cooled sidewalls of the condenser bag at some point in its passage through the condenser bag, instead of just flowing straight through the center of the condenser bag. Secondly, after the condenser bag has been operating for a short period of time, cooled condensate droplets become trapped on the screen material and these droplets will assist in causing even more moisture to condense out of the moist gas. The mesh helps increase the surface area on which condensation can occur.

Prior art condensers generally include both a cooling zone and a heating zone within the condenser unit. That coupling of the condensing function of the unit with a heating function within the same assembly reduces the flexibility of allowing the two functions to be manipulated independently of each other. Prior art condensers generally remove heat from the exhaust gas and then just allow the heat to dissipate into the environment.

In the disclosed condenser bag, those two functions, cooling and heating, are separate. The heating zone is not a part of the disclosed condenser bag. A disclosed embodiment includes the concept, for example, of taking the heat that is removed from the exhaust gas and using it to heat another component, such as the exhaust filter.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawing), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. A system for condensing moisture in a moist gas stream entering or leaving a bioreactor, the system comprising:
   a condenser container capable of holding a fluid, the condenser container comprising:
   an outer wall surface and an inner wall surface, the inner wall surface defining an interior chamber for holding the fluid;
   a first fitment attached to the condenser container, the first fitment forming a first port configured to allow the moist gas stream to flow through the first port and into the interior chamber;
   a second fitment attached to the condenser container, the second fitment forming a second port configured to allow a dried gas to flow from the interior chamber and out of the second port; and
   a cooling device in contact with at least one portion of the outer wall surface of the condenser container and arranged to cool the at least one portion of the outer wall surface of the condenser container, thereby condensing moisture in the moist gas stream entering or leaving the bioreactor,
   wherein the condenser container is arranged to provide a condenser flow path between the first and second fitments, the condenser flow path reducing the velocity of the gas stream flowing through the chamber;
   wherein the cooling device comprises a thermoelectric module comprising a first module surface and a second module surface, and wherein the thermoelectric module is configured for cooling the first module surface and transferring heat removed from the first module surface to the second module surface, wherein the first module surface is configured to provide cooling for the at least one portion of the outer wall surface of the condenser container; and
   wherein the second module surface is configured to assist in heating of a filter positioned downstream of the condenser container.

2. A method of condensing moisture in a gas stream leaving a bioreactor, the method comprising:
   providing a system according to claim 1;
   providing fluid communication of the first port of the condenser container with a port of the bioreactor arranged to allow the moist gas stream to leave the bioreactor;
   allowing the moist gas stream leaving the bioreactor to flow through the first port and into the interior chamber of the condenser container;
   cooling the at least one portion of the outer wall surface of the condenser container;

allowing heat to be transferred from the interior chamber of the condenser container to the cooling device, thereby lowering the temperature of the interior chamber of the condenser container;

condensing moisture in the moist gas stream; and forming a dry gas stream leaving the bioreactor.

3. A system for condensing moisture in a moist gas stream entering or leaving a bioreactor, the system comprising:

a condenser container capable of holding a fluid, the condenser container comprising:

an outer wall surface and an inner wall surface, the inner wall surface defining an interior chamber for holding the fluid;

a first fitment attached to the condenser container, the first fitment forming a first port configured to allow the moist gas stream to flow through the first port and into the interior chamber;

a second fitment attached to the condenser container, the second fitment forming a second port configured to allow a dried gas to flow from the interior chamber and out of the second port; and a cooling device in contact with at least one portion of the outer wall surface of the condenser container and arranged to cool the at least one portion of the outer wall surface of the condenser container, thereby condensing moisture in the moist gas stream entering or leaving the bioreactor, wherein the condenser container is arranged to provide a condenser flow path between the first and second fitments, the condenser flow path reducing the velocity of the gas stream flowing through the chamber;

wherein the condenser container is provided between a first plate and a second plate, wherein one or both of the first and second plates is connected to at least one cooling device;

wherein the condenser container is provided with a partition, the partition being a welded part in the condenser container and/or a compression provided to the condenser container by at least one bar provided to at least one of the first or second plates, said bar being arranged to provide the partition to the condenser container by compressing the condenser container against the other of the first or second plates wherein the partition comprises both the compression provided by the at least one bar and the welded part, said welded part being provided from a first side of the condenser container and provided inclined towards the compression from the bar such that the welded part and the compression together forms a partition from the first side of the condenser container towards the opposite second side of the condenser container, the inclination of the welded part providing an acceptance for different positioning of the condenser container between the first plate and the second plate when a condenser container is provided in the system with the first side of the condenser container protruding out above the first and second plates.

4. The system of claim 3, wherein the cooling device is arranged to be in contact with at least one portion of the outer wall surface of a front panel of the condenser container and at least one portion of the outer wall surface of a back panel of the condenser container.

5. The system of claim 3, wherein the cooling device comprises at least two thermoelectric modules, wherein at least one thermoelectric module is arranged to provide cooling to at least one portion of a front panel of the condenser container and at least one thermoelectric module is arranged to provide cooling to at least one portion of a back panel of the condenser container.

6. The system of claim 3, wherein the thermoelectric module is a Peltier heating and cooling module.

7. The system of claim 3, wherein tube holders are provided to an upper part of the system for holding tubes connected to the first and second fittings of the condenser container.

8. The system of claim 3, wherein the condenser container comprises a flexible bag.

9. The system of claim 3, wherein the system is disposable or single use.

10. The system of claim 3, wherein the partition is provided substantially in the middle of the container and starting at or close to a first side of the container towards an opposite second side of the container but not all the way to this opposite second side, thus leaving an open passage at the opposite second side.

11. The system of claim 10, wherein a condensate drain port is provided close to the opposite second side of the container.

12. The system of claim 10, wherein the first fitment is attached to the outer wall surface of the condenser container close to the first side of the container on one side of the partition and the second fitment is attached to the outer wall surface of the condenser container close to the first side of the container but on the other side of the partition.

13. The system of claim 12, wherein more than one first fitments are provided close to the first side of the container on one side of the partition and more than one second fitments are provided close to the first side of the container on the other side of the partition, the first and second fitments can be provided to either a front panel or a back panel of the container or to both a front panel and a back panel of the container.

14. The system of claim 3, further comprising a structure comprising a biocompatible material disposed within the interior chamber, the structure arranged to allow condensation to form thereon.

15. The system of claim 14, wherein the structure arranged to allow condensation to form thereon is also arranged to promote turbulence within the container.

16. The system of claim 14, wherein the structure arranged to allow condensation to form thereon comprises a mesh.

17. The system of claim 16, wherein the mesh is pleated.

18. A method of condensing moisture in a moist gas stream to form a dry gas for addition to a bioreactor, the method comprising:

providing a system according to claim 3;

providing fluid communication of the first port of the condenser container with the moist gas stream;

allowing the moist gas stream to flow through the first port and into the interior chamber of the condenser container;

cooling the at least one portion of the outer wall surface of the condenser container;

allowing heat to be transferred from the interior chamber of the condenser container to the cooling device, thereby lowering the temperature of the interior chamber of the condenser container;

condensing moisture in the moist gas stream; and forming a dry gas.

19. The method of claim 18, further comprising allowing the dry gas flowing out of the second port to flow into a bioreactor.

* * * * *